United States Patent [19]

Joshua

[11] Patent Number: 4,966,695
[45] Date of Patent: Oct. 30, 1990

[54] HIGH PRESSURE LIQUID CHROMATOGRAPHY COLUMN JACKET

[76] Inventor: Henry Joshua, 256 Woodward Ave., Staten Island, N.Y. 10314

[21] Appl. No.: 346,782

[22] Filed: May 3, 1989

Related U.S. Application Data

[63] Continuation-in-part of Ser. No. 152,328, Feb. 4, 1988, abandoned.

[51] Int. Cl.⁵ .............................................. B01D 15/08
[52] U.S. Cl. .................................. 210/198.2; 210/175;
210/659; 55/386; 165/74; 165/76; 165/137;
422/61; 422/70; 422/104
[58] Field of Search ............ 210/656, 635, 175, 198.2,
210/659; 55/67, 197, 386; 422/61, 70, 104;
165/74, 76, 137

[56] References Cited

U.S. PATENT DOCUMENTS

| | | | |
|---|---|---|---|
| 43,774 | 8/1864 | Jackman | 165/74 |
| 792,506 | 6/1905 | Doyle | 165/74 |
| 1,789,739 | 1/1931 | Gay | 165/74 |
| 1,817,978 | 8/1931 | Feldmeier | 165/74 |
| 2,044,069 | 6/1936 | Erbach | 165/137 |
| 2,350,976 | 6/1944 | Worn | 165/74 |
| 2,545,966 | 3/1951 | McQuilty | 165/74 |
| 2,737,369 | 3/1956 | Wheeler | 165/137 |
| 3,063,682 | 11/1962 | Greene | 165/137 |
| 3,342,333 | 9/1967 | Geiss | 210/94 |
| 3,440,864 | 4/1969 | Blume | 210/198.2 |
| 3,578,785 | 5/1971 | Patterson | 210/198.2 |
| 3,926,800 | 12/1975 | Stephens | 210/198.2 |
| 4,093,550 | 6/1978 | Stahl | 210/198.2 |
| 4,238,327 | 12/1980 | Liburdy | 210/198.2 |
| 4,314,602 | 2/1982 | Frederick | 165/74 |
| 4,444,625 | 4/1984 | Smith | 165/74 |
| 4,451,374 | 5/1984 | Peterson | 210/198.2 |
| 4,476,017 | 10/1984 | Scharft | 210/198.2 |
| 4,590,770 | 5/1986 | Howard | 165/74 |
| 4,637,347 | 1/1987 | Troy | 165/74 |
| 4,675,113 | 6/1987 | Graves | 210/198.2 |

*Primary Examiner*—Ernest G. Therkorn
*Attorney, Agent, or Firm*—Bernard Malina

[57] ABSTRACT

A high pressure liquid chromatography jacket includes a rectangular, fluid-tight enclosure which has a removable cover on which a pair of tubing seal fittings are mounted. The fittings form a fluid-tight seal around the inlet and discharge tubes of a chromatographic column which is mounted in the enclosure. The enclosure is connected to a source of temperature controlled fluid which circulates through the enclosure and controls the temperature of the chromatographic column.

In an alternative embodiment of the invention, a valve is provided which allows sample materials being loaded to enter a sample storage loop, which is exposed to the temperature controlled fluid. The sample, whose temperature has been controlled by the temperature controlled fluid, is then injected into a chromatographic column under high pressure.

17 Claims, 5 Drawing Sheets

FIG. IIA

FIG. IIB

HIGH PRESSURE LIQUID CHROMATOGRAPHY COLUMN JACKET

This is a continuation-in-part of may application Ser. No. 152,328 entitled High Pressure Chromatography Jacket, now abandoned.

BACKGROUND OF THE INVENTION

The advantages of temperature control of high pressure liquid chromatography columns are well known in the field of chromatography. Keeping column temperatures at clearly defined and reproducible levels eliminates an important variable in high pressure liquid chromatography. Temperature variations affect the reproducibility of chromatographic separations in regard to: retention times, peak height and selectivity, or order of elution of components.

The advantages of higher than ambient temperature in high pressure liquid chromatography include the following. The increased temperature results in decreased viscosity of eluents, causing a decrease in back pressure. A result of decreased back pressure is less wear on pumps and injection valves. Alternatively, an increase in flow is possible while retaining the pressure observed at a lower temperature. The increased temperature also results in increased resolution for a given analysis time or faster analysis time with identical resolutions obtained at lower temperature. Higher resolutions of components is due to more rapid equilibration at higher temperatures of solutes between stationary and moving phases. For reverse phase columns at increased temperatures, the composition of the eluent can be changed to a lower percentage of organic solvent. This adds up to significant financial savings especially in preparative work. At higher temperatures, one generally observes an increase in solubility of solutes. This allows a greater weight throughput per each injection.

Temperatures lower than ambient temperatures allow separation of conformational isomers which would rapidly interconvert at ambient or higher temperatures. Lower temperatures also allow the chromatography of temperature sensitive compounds without their decomposition or denaturation.

Optimum separations of components in a mixture subjected to chromatography is achieved when the high pressure liquid chromatography columns are at a uniform temperature cross sectionally and longitudinally. Achieving a uniform temperature is not a trivial matter when the desired separation temperature is non ambient. In this case the solvents used must be brought to the desired temperature before entering the column in order to prevent temperature gradients in the column. Another source for temperature inhomogeneities is the frictional heat generated by the resistance of column packing to the solvents which are pumped at high pressure (normally up to 5000 psi) through the high pressure liquid chromatography columns.

Ideally the apparatus used to control the temperatures of high pressure liquid chromatography columns should have the following characteristics:

The apparatus should accommodate columns of different dimensions with different end fittings and connecting tubing. High pressure liquid chromatography columns come in a variety of sizes from less than 1mm internal diameter and a few cm in length to very large preparative columns whose diameters may exceed 12" and whose length may reach several feet.

In the past, attempts have been made to achieve temperature control of high pressure liquid chromatography columns using; air ovens, heating blocks, foil heating elements, and column jackets.

In air oven devices heated air is circulated by an electric fan in a closed container which includes the high pressure liquid chromatography column. The air is heated by electrical resistance elements and the temperature is controlled by electronic heating regulators.

The disadvantages of air ovens include the risk that high pressure liquid chromatography columns may develop leaks of flammable high pressure chromatography column solvents being pumped at high pressure, especially when the column hardware is subjected to changes in temperature. These leaks are potential fire and explosion hazards in air ovens since the resistance elements may ignite the flammable solvents.

In order to accommodate a variety of column sizes and to accommodate heating elements, air fan and often flammable gas detectors in a single box, air ovens are generally bulky. Not only is the bulk of air ovens. inconvenient but more important they require the use of long connecting tubing between the injector valve and inlet of the high pressure liquid chromatography column and between the outlet of the column and the detector. This tubing causes mixing of separated components and thereby deteriorates the chromatographic process. This effect is especially pronounced when columns of small inner diameter are used (microbore columns).

The heat transfer capability of air is quite limited. Thus, heat transfer for flow rates used with analytical columns of up to two milliliter/minute may be sufficient to thermally equilibrate the incoming solvent. However, flow rates used for preparative chromatography are usually greater than two milliliter/minute. These flow rates are greater than could generally be thermally equilibrated in air ovens.

Achieving sub-ambient temperatures in an air oven adds additional complexity and bulk while adding problems due to condensation of water vapor and consequent corrosion.

Heating blocks are heated by electrical resistance elements and transmit their heat by close physical contact with high pressure liquid chromatography columns which are placed into matching cavities in the heating blocks.

Problems with heating blocks include the following. Cavities of different physical dimensions are required for each column of different size. Accommodating a wide variety of column sizes require the expense of preparing a large number of heating blocks with matching cavities and causes the inconvenience of having to store them until needed. Heating blocks generate "hot spots" when close physical proximity of the column and the walls of the cavity is not maintained uniformly over the column surface. Thus, temperature inhomogeneities may be observed in high pressure liquid chromatography columns heated with heating blocks. Accommodating the heating requirements of a wide range of flow rates (from 0.1 to 50 milliliter/min) while maintaining close temperature control is difficult to achieve with a heating block, in particular if the length and volume of inlet tubing is to be kept to a minimum. Heating blocks are also generally bulky in order to accommodate a variety of column sizes, heating elements and often flammable gas detectors. In addition, heating blocks are amenable only with difficulty to sub-ambient temperature control.

Foil heating elements are thin strips of heating elements which are wrapped directly around the high pressure liquid chromatography columns.

Problems with heating foils include the following. This method of temperature control requires different foils for different size columns. The heating foils are fragile. Removal of the foils and placing them on different columns is often accompanied by failure of the heating elements. Matching the energy requirements to the flow rate ranges used in high pressure liquid chromatography is difficult to achieve. Foil heating elements are not suitable for below-ambient temperature control.

Column jackets are generally cylindrical devices which have high pressure liquid chromatography columns concentrically positioned in them with seals for the column inlet and outlet tubing at opposite ends of the jackets. The jacket has also an inlet and outlet for circulating heat transfer fluid. Commercially available circulating water baths with or without refrigeration capabilities, are used to pump and control the temperature of the heat transfer fluid which is generally water with or without antifreeze.

The circulating water bath is connected to the column jacket usually with flexible hose such as rubber, or flexible plastic. The column jacket does not add appreciably to the bulk of the column since the circulating bath which provides the heating and/or cooling apparatus can be positioned some distance from the column jacket and high pressure liquid chromatography apparatus. The column, including its end-fittings and some of the inlet and outlet tubing, is totally immersed in the circulating heat transfer fluid. This, as well as the excellent heat transfer characteristics of a circulating fluid provides superior temperature equilibrations. In order to accommodate different column sizes the cylindrical part of the column jackets are usually made of different lengths and diameters whereas the end fittings and liquid seals can accommodate the different size cylinders. The dangers of fire and explosion of leaking flammable solvents are minimal since the solvents would leak into and be diluted by the heat transfer liquid.

Problems with conventional column jackets include the following. Conventional water jackets are often constructed of glass cylinders. Breakage of glass cylinders with concomitant spillage of heat transfer media can occur. Furthermore, water jackets occasionally suffer from leaks of the heat transfer fluid, either at the column connecting tubing seals or at the connections to the circulating heat transfer fluid.

Removal of high pressure liquid chromatography columns from conventional column jackets requires a number of operations which include drainage of the heat transfer fluid from the jacket and complete disconnection of one of the column connecting tubes in order to remove the column through the other cylindrical opening of the jacket. These steps must be repeated in reverse order when a column is to be properly connected. These operations become increasingly more difficult with increasing size of the high pressure liquid chromatography column.

A necessary element of high pressure chromatography system is a convenient means for inserting or injecting sample materials, whose components are to be separated, into the chromatographic column. It is especially desirable for this means to be capable of injecting a sample into the column without a need for disassembly of the column and without disturbing the thermal state of the material in the column.

OBJECTS OF THE INVENTION

It is an object of the present invention to overcome the disadvantages of the prior art by providing a high pressure liquid chromatography column jacket in which chromatography columns can be easily and conveniently installed and removed.

Another object of the present invention is to provide a high pressure liquid chromatography column jacket which can accommodate individual chromatography columns of different sizes.

Another object of the present invention is to provide a high pressure chromatography column jacket which can accommodate a plurality of chromatography columns simultaneously.

Another object of the present invention is to provide a high pressure liquid chromatography column jacket which minimizes the danger of fire and explosions during operation.

Another object of the present invention is to provide a high pressure liquid chromatography column jacket which is inherently reliable and safe to operate.

Another object of the present invention is to provide a high pressure liquid chromatography column jacket which is relatively compact in configuration.

Another object of the present invention is to provide a high pressure liquid chromatography column jacket which is capable of providing ready access to an internally mounted chromatography column.

Another object of the present invention is to provide a high pressure liquid chromatography column jacket which includes a valve for injection of sample materials into a high pressure chromatography column.

Another object of the present invention is to provide a high pressure chromatography column jacket which enables the injection of sample materials into a high pressure chromatography column which are at the same temperature as the material already inside the column.

Still another object of the present invention is to provide a high pressure liquid chromatography column jacket which has relatively few components, which is economical to manufacture, resulting in a relatively low unit cost.

Another object of the present invention is to provide a high pressure liquid chromatography column jacket which is operative to thermally equilibrate the pump eluent to the temperature of the temperature controlled liquid before entering the column.

Yet another object of the present invention is to provide a high pressure liquid chromatography column jacket which is capable of providing ready access to an internally mounted chromatography column without displacing the chromatography column.

SUMMARY OF THE INVENTION

In accordance with the present invention there is provided a high pressure liquid chromatography column jacket which comprises a rectangular box-like enclosure within which a high pressure liquid chromatography column may be mounted. The high pressure liquid chromatography column jacket includes a pair of end walls, a pair of side walls, a bottom wall, and a cover. The cover has a pair of tubing seals and one of the side walls has a pair of spaced apart hose connections. The cover is removably attached to the side walls and the end walls, by means of a plurality of screws which passes through the cover and through a gasket.

In use, connecting tubing for the chromatography column is passed through the tubing seals and sealed in place by tightening tubing seals. However, the tubing is movable when the seals are loosened whereby the cover of the column jacket can be moved without disturbing the chromatography column. The connecting tubing is connected to the high pressure liquid chromatography column in a conventional manner and the chromatography column is mounted in the enclosure. The cover is attached to the side and end walls by tightening the screws and the hose connections are connected to a source of temperature controlled fluid which circulates through the enclosure and controls the temperature of the chromatographic column.

In an alternative embodiment of the invention, a six port two position rotary valve is mounted within the high pressure liquid chromatography jacket. Two of the ports are connected to a loop of tubing which is also located within the high pressure liquid chromatography jacket. The valve allows a sample to be pumped into the tubing loop under low pressure where it attains a thermal condition which is isothermal relative to the material in the chromatography column, as a result of the action of the temperature controlled fluid which circulates through the enclosure. The valve, which is under the control of an operator, allows the sample material in the tubing loop to be injected into the chromatography column without a need for dismantling or reducing the pressure in the column.

BRIEF DESCRIPTION OF THE DRAWINGS

A fuller understanding of the present invention may be had by referring to the following specification and drawings in which.

DETAILED DESCRIPTION OF THE INVENTION

Figure 1:
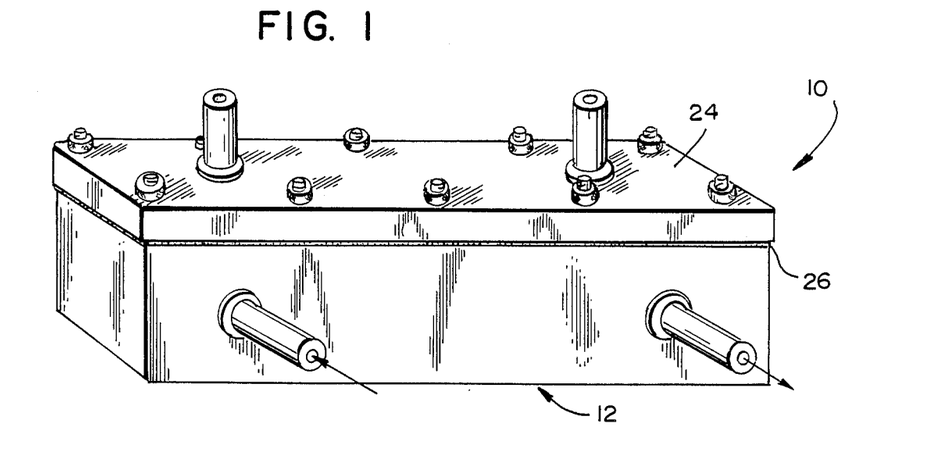
FIG. 1 is an overall perspective view of a high pressure liquid chromatography column jacket made in accordance with the present invention.
Figure 2:
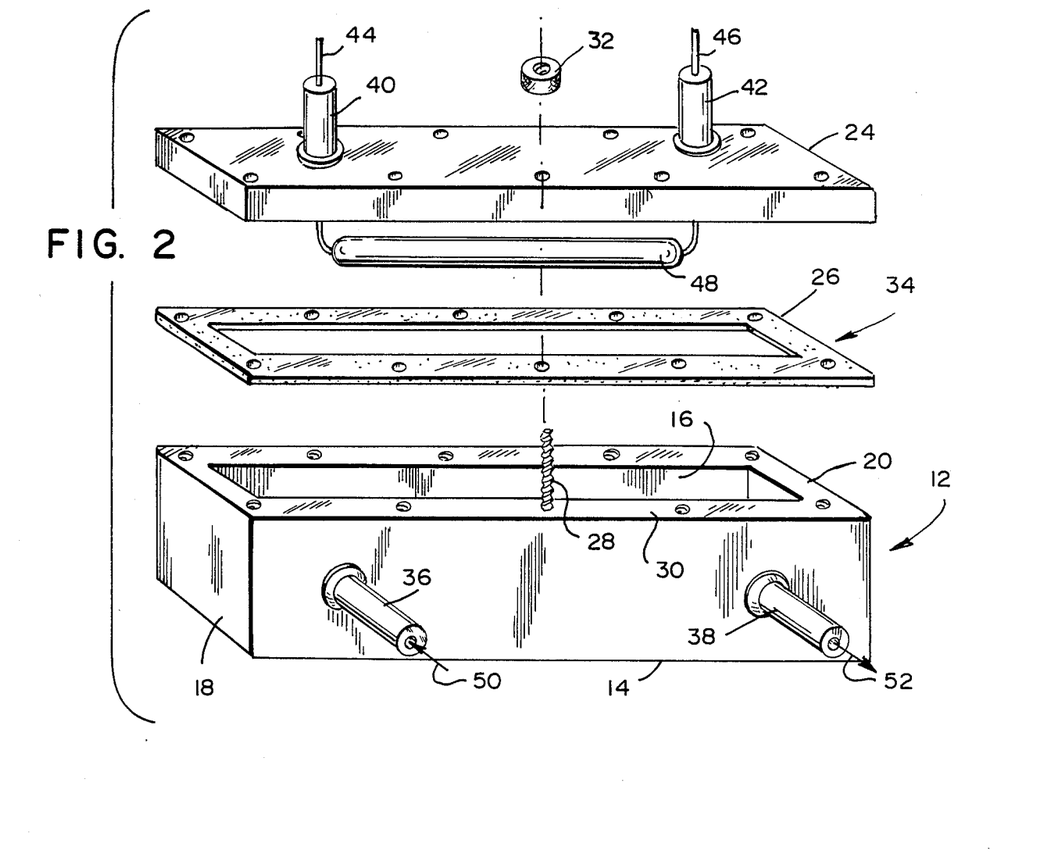
FIG. 2 is an exploded view of the apparatus of FIG. 1 showing a liquid chromatography column installed in the apparatus.
Figure 3:
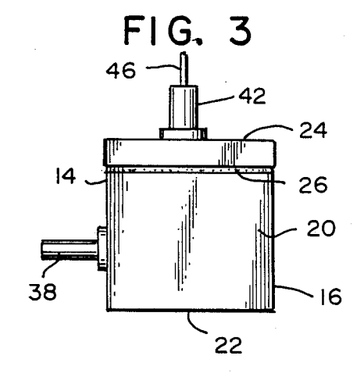
FIG. 3 is an end view of the apparatus of FIG. 1.

With reference to the drawings, there is shown in FIGS. 1, 2 and 3 a preferred embodiment of a high pressure liquid chromatography column jacket 10 made according to the present invention. In the preferred embodiment, the apparatus 10 according to the present invention includes a container 12 which is formed by a pair of spaced apart side panels 14, 16, a pair of spaced apart end panels 18, 20, and a bottom panel 22 and a cover 24 which is mounted on a gasket 26. The cover 24 is connected to the container 12 by a plurality of studs and knurled nuts which are shown typically as the stud 28 which projects from the upper surface 30 of the panel 14, and the knurled nut 32 which engages the stud 28. The panels 14, 16, 18, 20, 22, the cover 24, the gasket 26, and the plurality of studs 28 and knurled nuts 32 cooperate to form a rectangular fluid-tight enclosure 34.

The enclosure 34 may be described as a rectangular prism, a parallel piped or a box-like structure.

A pair of hose connection fittings 36, 38 are mounted on the panel 14 and a pair of tubing seal fittings 40, 42, or tubing seals, are mounted on the cover 24. The tubing seal fittings 40, 42 allow a fluid-tight seal to be formed around a pair of connecting tubes 44, 46 which, during the use of the apparatus 10, pass through the cover 24 as is shown in FIG. 2. The tubing seals 40, 42 are sized and of appropriate lubricity to permit sliding movement of tubes 44 and 46 within seals 40 and 42 respectively. Accordingly, column 48 need not be moved in order to permit cover 24 to be raised. The connecting tubes 44, 46 allow the passage of liquids into and out of a high pressure liquid chromatography column 48 which is connected to the tubes 44, 46, as is shown in FIG. 2. The high pressure liquid chromatography column 48 is conventional in nature and therefore the construction of the column 48 or the details of the chromatographic process need not be described in detail. The hose connection fittings 36, 38 and the tubing seal fittings 40, 42 are also conventional in nature and need not be described in detail.

In use, the hose connection fittings 36, 38 are connected to a source of thermally controlled fluid by means of a pair of hoses, which are not shown. The fluid flows into the apparatus according to the invention via one of the hose connection fittings 36 and is discharged from the apparatus 10 via the other hose connections fitting 38. The direction of flow of the fluid is shown by the arrows 50, 52 in FIG. 2. The fluid may be in the nature of water or another fluid which is appropriate for the desired range of temperatures. The temperature of the fluid may be controlled by any one of a number of conventional types of apparatus such as heater for temperatures above ambient, and refrigeration units for temperatures below ambient. The temperature control apparatus is conventional in nature and therefore need not be shown or described in detail.

The cover 24, the gasket 26, and the container 12 cooperate to form a fluid-tight enclosure or jacket which permits the thermally controlled fluid to flow around the high pressure chromatography column 48 and thereby closely control its temperature.

The cover 24 and the container 12 are preferably made of a transparent material such as plastic, thereby enabling a user to easily inspect the high pressure chromatography column 48. When the cover 24 is removed, the high pressure chromatography column 48 remains attached to the cover 24, as is shown in FIG. 2. This facilitates detailed inspection, repair, replacement, or repacking of the column 48.

It is also feasible to manufacture the cover 24 and the container 12 of metal.

Figure 4:
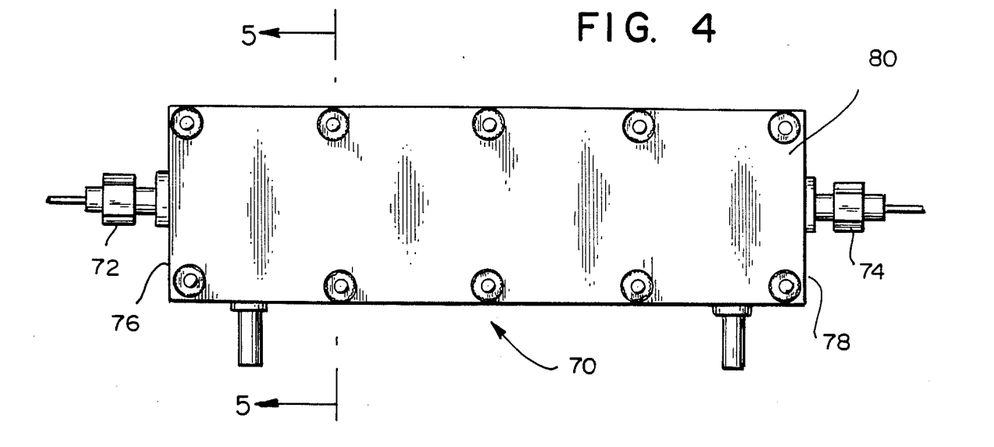
FIG. 4 is a plan view of an alternative embodiment of the apparatus of FIG. 1.
Figure 5:
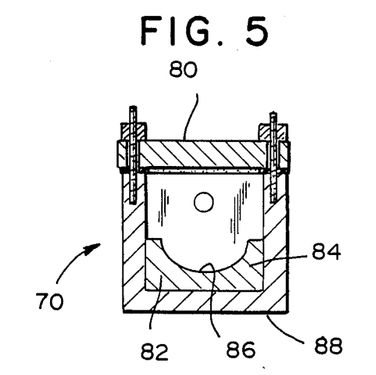
FIG. 5 is a cross-sectional view taken along the line 5—5 in FIG. 4.

In an alternative embodiment of the invention 10, which is shown in FIGS. 4 and 5, the tubing seal fittings 72, 74 are mounted on the end panels 76, 78 instead of on the cover 80. This embodiment 70, which may be used with large and heavy chromatographic columns, includes at least one chromatographic column support 82. The chromatographic column support 82 is in the form of a plate-like member 84. A semi-circular surface 86, which is proportioned to fit a cylindrical chromatographic column, is mounted on the bottom panel 88. In this embodiment, the removal of cover 80 is further facilitated since tubes 44 and 46 do not pass through cover 80.

Figure 6:
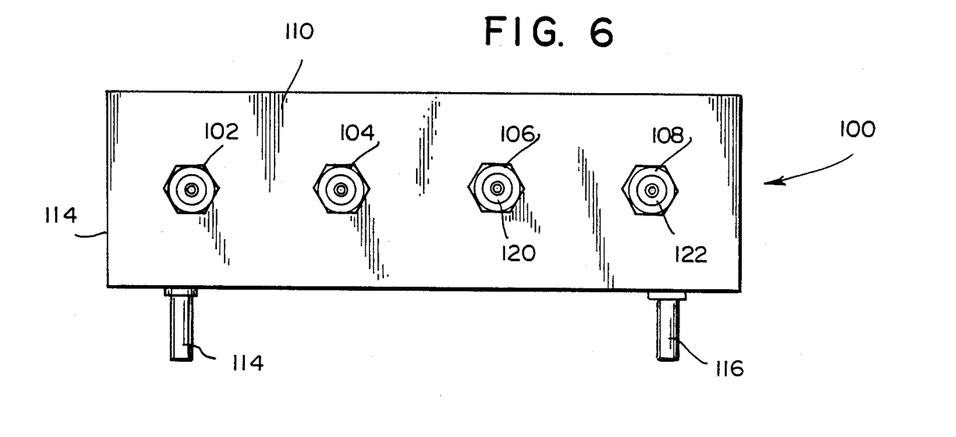
FIG. 6 is a plan view of another alternative embodiment of the apparatus of FIG. 1.
Figure 7:
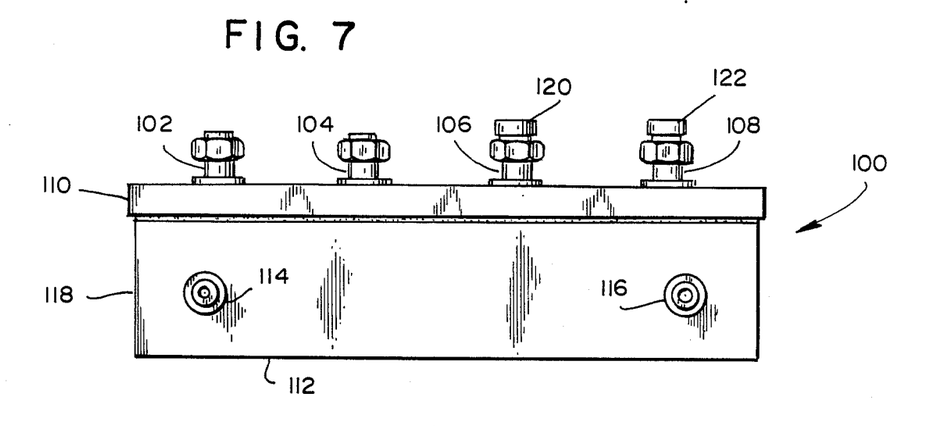
FIG. 7 is an elevation view of the apparatus of FIG. 6.

In another alternative embodiment of the invention 100 which is shown in FIGS. 6 and 7, a plurality of tubing seal fittings 102, 104, 106, 108 are provided, mounted in a linear array on the cover 104. The container 112 is similar to the container 12, which has been previously described and includes hose connection fittings 114, 116 which are similar to the hose connection fittings 36, 38. This embodiment 100 facilitates the use of the single jacket 100 for a range of chromatographic columns of different lengths. The jacket 100 has the advantage of not requiring any change in the conventional tubing or hardware to be made on a conventional chromatographic column in order to accommodate the use of the jacket 100. In this embodiment 100, the tubing seal fittings 102, 104, 106, 108 are adapted for either providing a fluid-tight seal around a connecting tube when the tube is passed through the tubing seal fittings 102, 104, 106, 108, or providing a fluid tight seal against leakage from the enclosure 114 when no tubes are passed through the tube seal fittings 102, 104, 106, 108. This feature, which may be in the nature of a removable cap, such as the caps 120, 122 for fittings 106, 108 may be unused during the installation of a particular chromatographic column.

Figure 8:
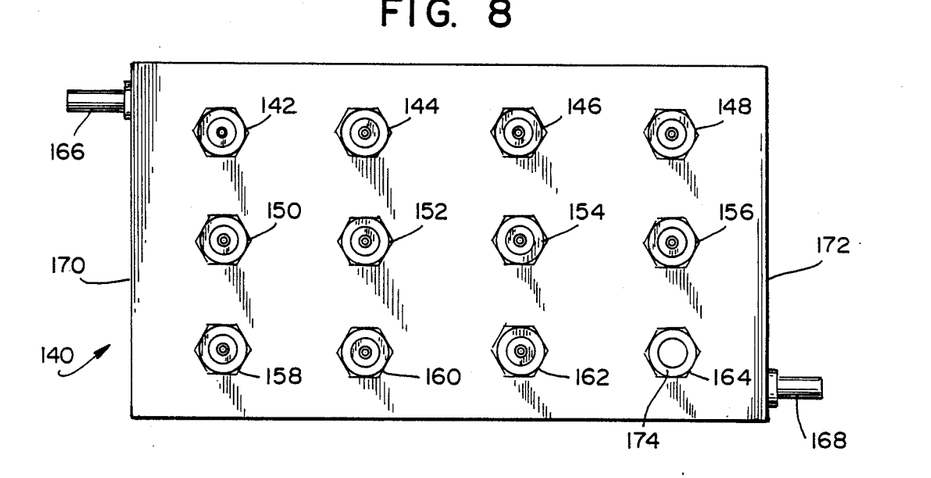
FIG. 8 is still another alternative embodiment of the apparatus of FIG. 1.
Figure 9:
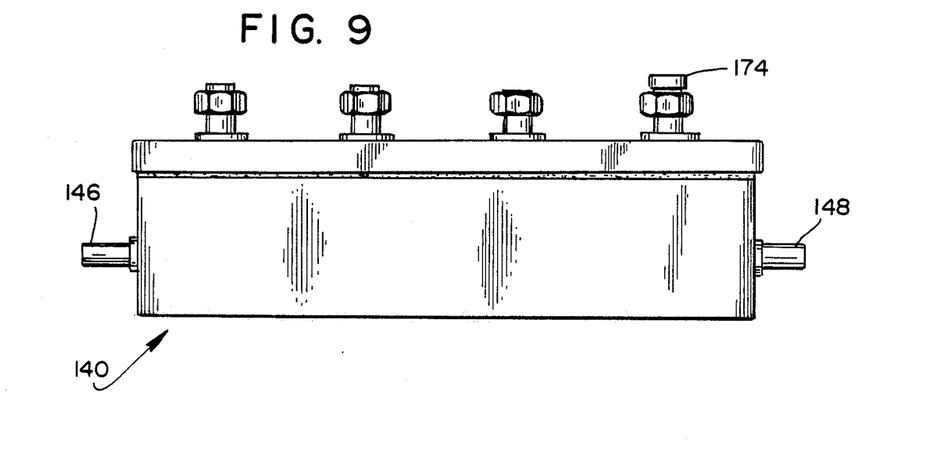
FIG. 9 is an elevation view of the apparatus of FIG. 8.

In still another alternative embodiment of the invention 140, which is shown in FIGS. 8 and 9, a plurality of tubing seal fittings 142, 144, 146, 148, 150, 152, 154, 156, 158, 160, 162, 164 are provided mounted in a grid array and the hose connection fittings 166, 168 are mounted on the end panels 170, 172. This embodiment 140 facilitates the use of a single jacket to control the temperature of a plurality of chromatographic columns. The chromatographic columns may be of identical length or may be of various lengths and since the thermally controlled fluid flows past each of the columns, all of the columns are maintained at the same temperature.

As in the previous embodiment 100, the tubing seal fittings 142, 144, 146, 148, 150, 152, 154, 156, 158, 160, 162, 164 are adapted for either providing a fluid-tight seal around a connecting tube when the tube is passed through the tubing seal fittings 142, 144, 146, 148, 150, 152, 154, 156, 158, 160, 162, 164, or providing a fluid-tight seal against leakage from the enclosure 174 when no tubes are passed through the tubing seal fittings. As previously described, this feature may be in the nature of a removable cap such as the cap which is shown typically as the cap 174 shown mounted on the fitting 164. In use, a plurality of caps, similar to the cap 174, are mounted on any of the tubing seal fittings which may be unused during the installation of a particular arrangement of chromatographic columns.

The jacket 140 may be used to control the temperature of an individual chromatographic column or alternatively a plurality of chromatographic columns may be installed in the jacket. The plurality of chromatographic jackets may be connected individually, in series or in parallel in order to achieve the desired separation process.

Figure 10:
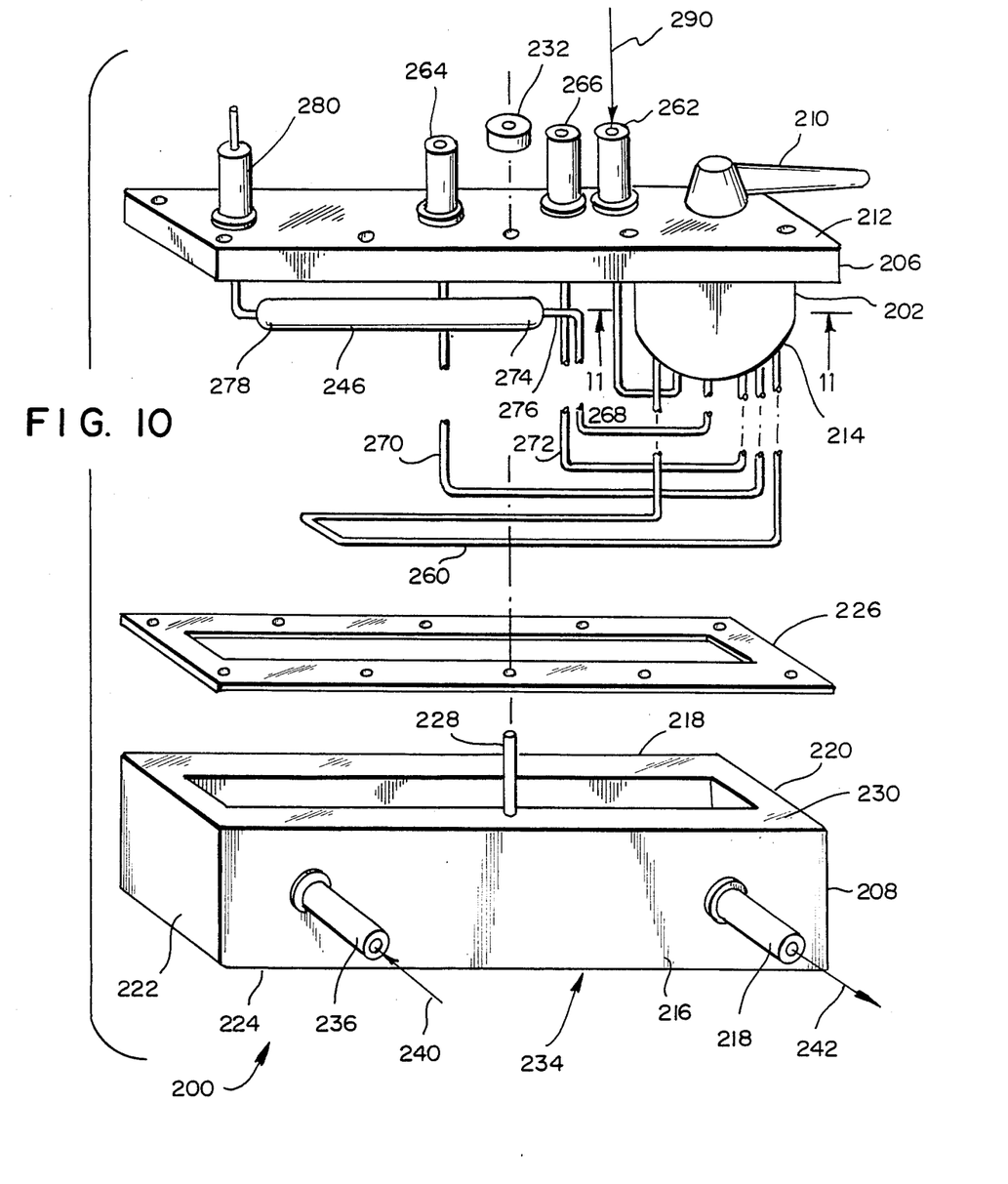
FIG. 10 is an exploded view of an alternative embodiment of the apparatus of FIG. 1 which includes an internally mounted valve.
Figure 11A:
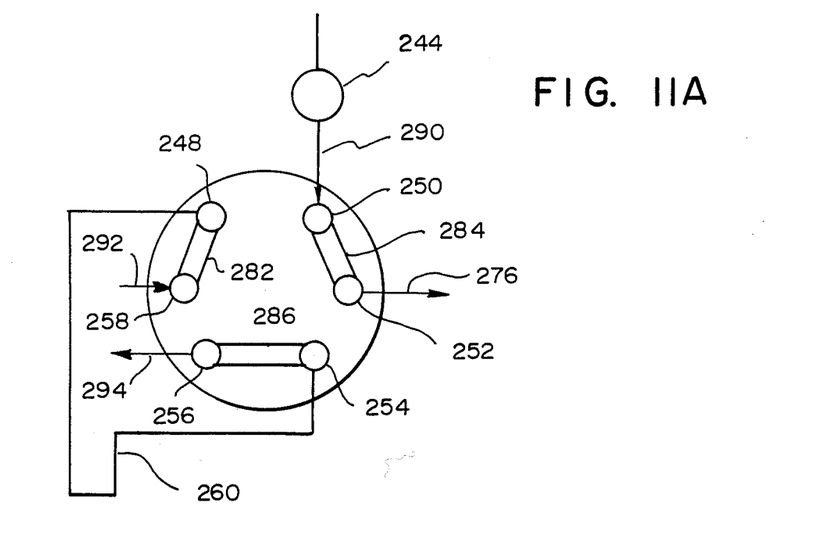
FIG. 11A is a schematic view of the valve of FIG. 10 with the valve positioned for loading sample material into the apparatus.
Figure 11B:
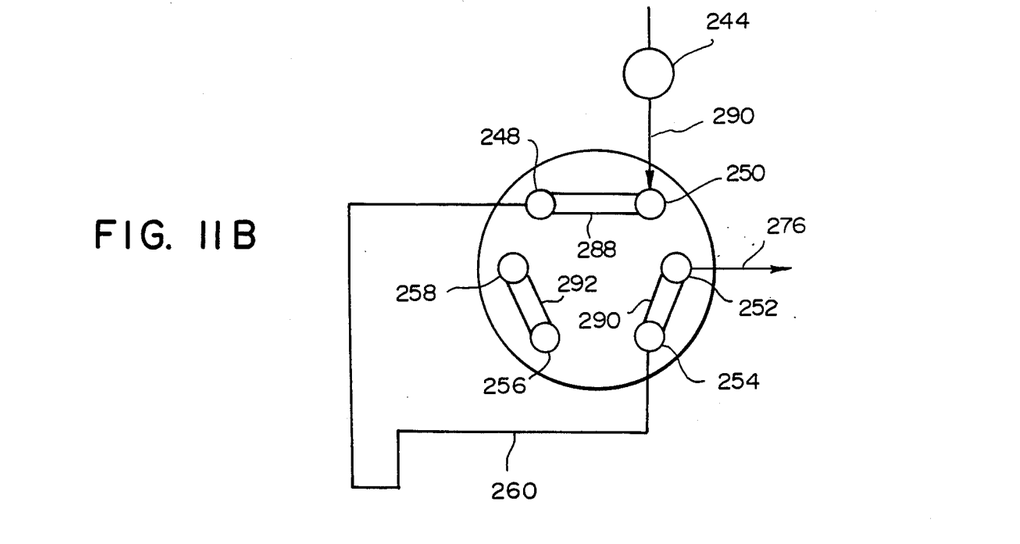
FIG. 11B is a schematic view of the valve of FIG. 10, similar to FIG. 11A with the valve positioned for injecting the sample material into the chromatography column.

In an alternative embodiment 200 of the invention shown in FIGS. 10, 11A and 11B, a six port two-position valve 202 is mounted on the cover 206 of the container 208. The valve 202 is operated by means of an operating handle 210 which is mounted on the outside surface 212 of the cover 206. The operating handle 210 and the valve body 214 are connected by a valve stem which passes through a seal fitting, both of which are not shown.

In a manner which is similar to that which has been described in connection with FIG. 1, the container 208 is formed by a pair of spaced apart side panels 216, 218, a pair of spaced apart end panels 220, 222, and a bottom panel 224 and the cover 206 which is mounted on a gasket 226. The cover 206 is connected to the container 208 by a plurality of studs and knurled nuts which are shown typically as the stud 228 which projects from the upper surface 230 of the panel 216, and the knurled nut 232 which engages the stud 228. The panels 216, 218, 220, 222, 224, the cover 206, the gasket 226, and the plurality of studs 228 and knurled nuts 232 cooperate to form a rectangular fluid-tight enclosure 234.

A pair of hose connection fittings 236, 238 are mounted on the panel 216 and are connected to a source of thermally controlled fluid by means of a pair of hoses, which are not shown. The fluid flows into the apparatus according to the invention via one of the hose connection fittings 236 and is discharged from the apparatus 200 via the other hose connection fitting 238. The direction of flow of the fluid is shown by the arrows 240, 242 in FIG. 10. The fluid may be in the nature of water or another fluid which is appropriate for the desired range of temperatures. The temperatures of the fluid may be controlled by any one of a number of conventional types of apparatus such as heaters for temperatures above ambient, and refrigeration units for temperatures below ambient. The temperature control apparatus is conventional in nature and therefore need not be shown or described in detail.

The cover 206, the gasket 226, and the container 208 cooperate to form a fluid-tight enclosure 234 or jacket which permits the thermally controlled fluid to flow around the high pressure chromatography column 246 and thereby closely control its temperature.

The ports of the valve 202 have been numbered for reference as 248, 250, 252, 254, 256, 258. The internal and external connections of the ports 248, 250, 252, 256, 258 have been shown schematically in FIGS. 11A and 11B. The valve 202 has a first position or loading position, in which the ports 248 and 254 are connected to a length of tubing 260 which is formed into a loop configuration as is shown in FIG. 10. Ports 250, 256 and 258 connected to tubing seal fittings 262, 264, 266 which are mounted on the cover 206 of the enclosure 234. The ports 250, 256 and 258 are connected to the tubing seal fittings 262, 264, 266 via the tubes 268, 270, 272.

Port 252 is connected to the first end 274 of the high pressure chromatography column 246 via the tube 276. The column 246 is generally similar to the column 48 which has been described in FIG. 2. The second end 278 of the column 246 is connected to the tube seal fitting 280 which is mounted in the cover 206.

In the first position or loading position of the valve 202 shown in FIG. 11A, the ports 248 and 258 are connected via an internal valve passage 282, the ports 250 and 252 are connected by internal valve passage 284, and the ports 254 and 256 are connected by the internal valve passage 286.

In the second position or injection position of the valve 202 shown in FIG. 11B, the ports 248 and 250 are connected by internal valve passage 288, the ports 252 and 254 are connected by an internal valve passage 290, and the ports 256 and 258 connected by the internal valve passage 292.

Although the tubing 260 which serves to receive and store the sample materials has been shown as a single loop, it should be understood that this has been down for purposes of clarity of illustration and it is understood that a plurality of loops may be formed in the tube 260 to obtain the desired storage volume and heat transfer characteristics.

In use, the valve 202 is placed in the first, or loading position, FIG. 11A, and the tube fitting 262 is connected to a pump 244 which allows pressurized eluent to flow in the direction shown by the arrow 290 directly from the port 250 to the port 252 via the passage 284 and directly into the column 246 via the tube 276.

A sample, which is to be subjected to analysis, may at this time be introduced into the port 258 and into the tubing loop 260 under relatively low pressure flowing in the direction shown by the arrow 292 in FIG. 11A. Fluid which has been displaced from the tubing loop 260 leaves the apparatus 200 via the port 260 in the direction shown by the arrow 294 in FIG. 11A. The action of the thermostatically controlled fluid brings the sample material in the tubing loop 260 into thermal equilibrium with the eluent in the chromatographic column 246. The temperature of the valve body 214 itself is also controlled by the thermostatically controlled fluid, thereby reducing potential temperature variations between the sample material and the eluent.

The length of tubing 268 may be selected so that the eluent being pumped will be thermally equilibrated before entering port 250. Sample dilution, which would otherwise occur if long tubing for thermal equilibrium were used between injection valve 202 and column 246, is thereby avoided.

After a suitable time period has elapsed for the sample material in the tubing loop 260 to have attained the desired thermally equilibrium, an operator placed the valve 202 in the second or injection position shown in FIG. 11B. In this injection position the tubing loop 260 is connected to the column 246 via the ports 248, 252, 254 and passages 290. The port 248 is connected to the port 250 via the passage 288 allowing the pump 244 to inject the sample material directly into the column 246.

The apparatus 200 is thus able to inject sample material into the chromatographic column 246 in an efficient manner without disturbing the thermal equilibrium of the column 246, and without a need to depressurize or dismantle the column 246. The column 246 is attached to the cover panel 206 in a manner which has been previously described in connection with FIG. 1 and can therefore be removed for inspection in a rapid and cost effective manner.

Where a large chromatographic column is involved, it is advantageous to mount the injection valve on the end panels 220 or 222 or side panels 216 or 218 rather than on the cover 206.

Although preferred embodiments of the invention have been shown and described in detail, it is obvious that changes may be made in such detail of construction without altering the spirit and scope of the invention.

What is claimed is:
1. A high pressure liquid chromatography column apparatus comprising
   open container means,
   removable cover means proportioned to fit said container means,
   sealing means capable of forming a liquid-tight seal between said container means and said cover means, thereby forming enclosure means,
   attachment means for removably attaching said cover means and said container means,
   a pair of hose connection means mounted on said enclosure,
   at least one pair of tubing seal fittings mounted on said enclosure means,
   a chromatographic column means connected to said tubing seal fittings, said tubing seal fittings being mounted on said cover means, and a source of thermally controlled fluid for flowing through said hose connection means.

2. A high pressure liquid chromatography column apparatus, according to claim 1, in which said sealing means comprises gasket means.

3. A high pressure liquid chromatography column apparatus, according to claim 1, in which said attachment means comprises a plurality of studs mounted on said container means and a plurality of nuts cooperating with said studs to removably mount said cover means on said container means.

4. A high pressure liquid chromatography column apparatus, according to claim 1, in which said container means has the general configuration of a rectangular parallel piped.

5. A high pressure liquid chromatography column apparatus, according to claim 1, in which said hose connection means are mounted on said container means.

6. A high pressure liquid chromatography column apparatus, according to claim 1, in which said hose connection means are mounted on said cover means.

7. A high pressure liquid chromatography column apparatus, according to claim 1, in which said tubing seal fittings comprises a linear array of tube sealing connections.

8. A high pressure liquid chromatography column apparatus, according to claim 1, in which said tubing said fittings comprises a grid array of tube sealing connections.

9. A high pressure liquid chromatography column apparatus, according to claim 1, in which said enclosure means is made of a transparent material.

10. A high pressure liquid chromatography column apparatus, according to claim 1, in which said enclosure means is made of clear plastic.

11. A high pressure liquid chromatography column apparatus, according to claim 1, further comprises column support means mounted in said enclosure means.

12. A high pressure liquid chromatography column apparatus, according to claim 11, in which said column support means comprises at least one support member having a semi-circular surface.

13. A high pressure liquid chromatography column apparatus, according to claim 1, in which said enclosure means is made of metal.

14. A high pressure liquid chromatography column apparatus according to claim 1 further comprising
    sample storage means mounted in said open container means, valve means mounted in said open container means, with said valve means capable of a first position and a second position, first fluid port means, second fluid port means, pressure source means connected to said first fluid port means, fluid connection means mounted in said open container means with said fluid connection means selectively connected to said chromatographic column means, to said sample storage means, to said first fluid port means, and to said second fluid port means under the control of said valve means, with said first position of said valve means controlling said fluid connection means for connection of said chromatographic column connection means to said first fluid port means for pressurization of said chromatographic column means and controlling said fluid connection means for connection of said sample storage means to said second fluid port means for the purpose of loading of sample materials into said sample storage means, and with said second position of said valve means controlling said fluid connection means for connection of said sample storage means to said chromatography column means and to said first fluid port means for injection of said sample materials into said chromatographic column.

15. A high pressure liquid chromatographic column apparatus according to claim 14 in which said sample storage mans comprises tube means.

16. A high pressure liquid chromatographic column apparatus according to claim 14 in which said valve means comprises valve body means and operating handle means, with said valve body means mounted in said container means and with said operating handle means mounted externally on said container means.

17. A high pressure liquid chromatography column apparatus according to claim 16 in which said operating handle means and said valve body means are mounted on said removable cover means.

* * * * *